(12) United States Patent
Inoue et al.

(10) Patent No.: US 6,903,335 B1
(45) Date of Patent: Jun. 7, 2005

(54) ION ACTIVITY-MEASURING DEVICE AND METHOD FOR PRODUCING THE SAME

(75) Inventors: Toshihisa Inoue, Kyoto (JP); Takeshi Sakura, Kyoto (JP); Norimasa Noda, Kyoto (JP)

(73) Assignee: Arkray, Inc., Kyoto (JP)

(*) Notice: Subject to any disclaimer, the term of this patent is extended or adjusted under 35 U.S.C. 154(b) by 0 days.

(21) Appl. No.: 09/701,962

(22) PCT Filed: Jun. 4, 1999

(86) PCT No.: PCT/JP99/03013
§ 371 (c)(1),
(2), (4) Date: Mar. 5, 2001

(87) PCT Pub. No.: WO99/64849
PCT Pub. Date: Dec. 16, 1999

(30) Foreign Application Priority Data

Jun. 5, 1998 (JP) .......................................... 10-158129
Oct. 2, 1998 (JP) .......................................... 10-296105

(51) Int. Cl.$^7$ ............................................. G01N 27/30
(52) U.S. Cl. ..................... 250/290; 250/293; 250/294
(58) Field of Search ................................ 250/290, 294, 250/293, 281

(56) References Cited

U.S. PATENT DOCUMENTS

| | | | |
|---|---|---|---|
| 4,053,382 A | | 10/1977 | Maruyama et al. |
| 4,171,246 A | * | 10/1979 | Hamblen et al. ......... 205/778.5 |
| 4,655,899 A | * | 4/1987 | Saito et al. .................. 204/412 |
| 4,713,165 A | * | 12/1987 | Conover et al. ........ 204/403.05 |
| 4,789,435 A | | 12/1988 | Seshimoto et al. |
| 4,952,266 A | | 8/1990 | Tsuruta et al. |
| 5,516,703 A | * | 5/1996 | Caldwell et al. ............ 436/532 |
| 5,520,968 A | * | 5/1996 | Wynne et al. |
| 5,626,740 A | * | 5/1997 | Seto et al. ................... 141/130 |
| 6,004,442 A | * | 12/1999 | Choulga et al. ............ 204/416 |

FOREIGN PATENT DOCUMENTS

| | | |
|---|---|---|
| EP | 0 539 012 A2 | 5/1993 |
| JP | 58-004981 | 1/1983 |
| JP | 58-48844 | 3/1983 |
| JP | 58-102147 | 6/1983 |
| JP | 58-140635 | 8/1983 |
| JP | 58-193449 | 11/1983 |
| JP | 58-201056 | 11/1983 |
| JP | 58-211648 | 12/1983 |
| JP | 59-004659 | 1/1984 |
| JP | 61-22247 | 1/1986 |
| JP | 62-39758 | 2/1987 |
| JP | 6-288960 | 1/1994 |

OTHER PUBLICATIONS

Suppplementary European Search Report, EP 99 92 3924, Kyoto Daiichi Kagaku Co., dated May 30, 2001.
European Patent Office, Patent Abstract of Japan, *Measuring Apparatus of Ion Activity*, Fuji Photo Film Co Ltd., publication No. 58186039, publication date Oct. 29, 1983.

* cited by examiner

*Primary Examiner*—John R. Lee
*Assistant Examiner*—Anthony Quash
(74) *Attorney, Agent, or Firm*—Kilpatrick Stockton, LLP (57) ABSTRACT

The ion activity-measuring device of the present invention is provided with a hydrophobic bridge of which portion contacting with a liquid reservoir is hydrophilic. The hydrophobic bridge is made of, for example, at least one selected from the group consisting of polyester, nylon, polypropylene, rayon and polyethylene, and is produced by treating a portion contacting with the liquid reservoir with a spreading accelerator. The spreading accelerator is at least one selected from the group consisting of a surfactant and a hydrophilic polymer. There is also provided a method for producing the above ion activity-measuring device, comprising embedding nonwoven fabric in the cover plate to bond the nonwoven fabric to the cover plate.

7 Claims, 4 Drawing Sheets

ION ACTIVITY-MEASURING DEVICE AND METHOD FOR PRODUCING THE SAME

TECHNICAL FIELD

The present invention relates to an ion activity-measuring device, which is for measuring activity of an ion in a liquid sample such as blood, and a method for producing the same.

BACKGROUND ART

As a measurement device for measuring activity of an ion in a liquid sample by potentiometry, those utilizing dry-type electrodes are widely used.

Such ion activity-measuring devices have at least one pair of electrodes, one of the electrodes being to contact with a liquid sample, and the other being to contact with a reference liquid. The electrode to be contact with the liquid sample is usually imparted with an ion-selective property. When a liquid sample and a reference liquid are brought into contact with the electrodes, the potential difference generated between the electrodes depending on the difference of ion activity is measured, and this potential difference is converted into a concentration.

In order to generate such a potential difference, it is necessary to provide electric conduction between the liquid sample and the reference liquid, and this is realized by providing a bridge between a liquid reservoir for the liquid sample and a liquid reservoir for the reference liquid.

Examples of such a bridge include the slit bridge formed by a Groove such as one disclosed in Japanese Patent Publication (Kokoku) No. 58-4981, in the three-layer trilaminate bridge made of a porous layer inserted between hydrophobic coating film layers such as one disclosed in Japanese Patent Publication No. 59-4659, the shield type bridge which is a porous bridge composed of regions partitioned by shields that block diffusion of liquid such as one disclosed in Japanese Patent Application Laid-Open (Kokai) No. 58-201056, the thread bridge made of twisted yarn such as one disclosed in Japanese Patent Application Laid-Open No. 58-211648 and so forth.

DISCLOSURE OF THE INVENTION

As a result of researches of the present inventors, it was found that reproducibility of ion activity measurement utilizing the conventional devices still had a room for improvement.

Therefore, an object of the present invention is to provide an ion activity-measuring device that can improve reproducibility of ion activity measurement utilizing it.

The present inventors found that reproducibility of the ion activity measurement utilizing an ion activity-measuring device was improved by employing a bridge of a specific structure in the ion activity-measuring device. Thus, they accomplished the present invention.

The present invention provides an ion activity-measuring device for measuring activity of an ion in a sample, which comprises a hydrophobic bridge of which portion contacting with a liquid reservoir is hydrophilic (henceforth also referred to the "ion activity-measuring device of the present invention").

In the ion activity-measuring device of the present invention, the hydrophobic bridge is preferably produced from at least one selected from the group consisting of polyester, nylon, polypropylene, rayon and polyethylene.

Further, the hydrophobic bridge is preferably produced by treating the portion contacting with the liquid reservoir with a spreading accelerator.

The spreading accelerator is preferably at least one selected from the group consisting of a surfactant and a hydrophilic polymer.

In one embodiment of the ion activity-measuring device of the present invention, the aforementioned liquid reservoir is formed by bonding a cover plate and a substrate, at least one of which has a resist film having a liquid reservoir form, and the aforementioned hydrophobic bridge is made of nonwoven fabric.

The present invention also provides a preferred method for producing the ion activity-measuring device of the present invention according to the aforementioned embodiment. This production method comprises embedding the nonwoven fabric in the cover plate to bond the nonwoven fabric to, the cover plate. The nonwoven fabric and the cover plate are preferably bonded by ultrasonic fusion, more preferably knurling fusion.

BEST MODE FOR CARRYING OUT THE INVENTION

Hereafter, embodiments of the present invention will be explained in detail.

The ion activity-measuring device of the present invention measures ion activity based on the potentiometry. That is, the ion activity-measuring device of the present invention has at least one pair of electrodes, and when a sample and a reference liquid contact with the electrodes, a potential difference is generated between the-electrodes depending on the difference of ion activity. This potential difference is converted into the activity based on a calibration curve.

As the sample, liquid samples such as whole blood, blood serum, blood plasma and urine can be mentioned.

The ion activity-measuring device of the present invention can be constituted as a conventional ion activity-measuring device using dry-type electrodes except that it has a bridge of the specific structure.

Such an ion activity-measuring device generally comprises a first electrode, a first liquid reservoir which is disposed on the first electrode, a second electrode, a second liquid reservoir which is disposed on the second electrode, and a bridge that can provides electric conduction between the first liquid reservoir and the second liquid reservoir. It is stored in a dry state, and once a liquid sample and a reference liquid are put into the two liquid reservoirs when the device is used, electric conduction is attained between the first liquid reservoir and the second liquid reservoir by the bridge.

The electrodes can be formed by providing, on a substrate, metal layers for electrodes of a pattern composed of an electrode portion contacting with a liquid sample or a reference liquid, a terminal portion for electrically connecting with an apparatus for ion activity measurement and a lead wire portion connecting the electrode portion and the terminal portion; forming a resist film by printing or the like so that the electrode portion should be defined; chemically treating the electrode portion of each of the metal layers to form a metal salt layer; and providing an electrolyte layer and an ion selective film on each electrode portion defined by the resist film as required. Two or more of electrode pairs which each are composed of the first electrode and the second electrode may be provided.

As the substrate, a film or sheet of an insulating material, for example, a plastic film is used. As the plastic, polyester, polypropylene, acrylate resin, vinyl chloride resin and so forth are preferred.

As the metal for electrodes, metals such as silver, gold, platinum and palladium can be used, and silver is preferred. The electrode metal layer can be formed by a usual method, for example, screen printing utilizing a metal paste, metal vapor deposition and so forth.

The resist film is a layer made of an insulating material, and it is formed so that it should cover the portions other than the electrode portions and the terminal portions. When the electrolyte layer and the ion selective film are formed on the electrode portions in the subsequent steps, the resist film acts as a "wall" defining them. The "wall" is advantageously positioned outside the outer peripheries of the electrode portions by 0.2 to 1.0 mm to provide a gap, in order to form a uniform ion-selective film (refer to Japanese Patent Application Laid-Open No. 2-287146). By providing a non-conductive portion at the contact portion of the resist film and the electrode portions before forming the resist film, the same effect can be obtained as obtained by providing a gap between the Mwallo and the electrode portions. Although commercially available insulating inks and so forth can be used as a material of the non-conductive portion, non-conductive metal pastes are preferred in views of adhesive property, etching resistance and so forth. The non-conductive paste means a metal paste containing metal at such a content that the metal paste should not become substantially conductive.

While the material of the resist film is not particularly limited so long as it is an insulating material, commercially available insulating inks can be used. Examples thereof include those of ultraviolet curing type, for example, ML25089, ML25094 and ED450SS (trade names) produced by Acheson Japan, STR5320 (trade name) produced by Sinto Chemitron, DS-4 and INS-3 (trade names) produced by Jujo Chemical, FOC-3S (trade name) produced by Taiyo Ink Mgf., those of thermosetting type, for example, STR-5110 (trade name) produced by Sinto Chemitron, HIPET9300 (trade name) produced by Jujo Chemical, CR420G and CR48G (trade names) produced by Osaka Asahi Chemical and so forth.

When an ultraviolet curing type insulating ink is used, the resist film can be obtained by applying the insulating ink by screen printing, then curing it by ultraviolet irradiation using a UV irradiation machine, and repeating such procedure until a predetermined thickness is obtained. When a thermosetting type insulating ink is used, it may be heated to 100 to 150° C. instead of the ultraviolet irradiation.

The electrode portions defined by the resist film are chemically treated to form a metal salt layer on the metal surface. Before applying the resist, the metal terminal portions may be masked and chemically treated. The metal salt is usually a halide, preferably a chloride. However, other salts may also be used.

Then, the electrolyte layer and the ion-selective film are formed on each of the electrode portions utilizing the regions surrounded by the resist film. The electrolyte layer may not be used as the electrode disclosed in Japanese Patent Application Laid-Open No. 57-106852.

When an electrolytic solution is poured into this region, a liquid film of a substantially uniform thickness can be formed on the electrode by surface tension. Therefore, by drying the liquid without disturbing the liquid, an electrolyte layer of a uniform thickness can be formed at least on the reference electrode. Although the electrolyte is preferably one containing anions of the same species as that of the aforementioned metal salt, it may be one containing different anions, or an electrolyte layer not containing electrolyte may be formed only with a polymer.

Further, by pouring a solution of a material of the ion-selective film on the electrolyte layer and drying it, an ion-selective film of a uniform thickness can similarly be formed. The material of the ion-selective film may be a known one, for example, the hydrophobic ion-selective film material disclosed in Japanese Patent Publication No. 58-4981 can be used. When two or more electrode pairs are provided, different kinds of the ion-selective film materials can be used for the electrode pairs, and thus it is enabled to simultaneously measure activities for two or more kinds of ions.

The liquid reservoir is not particularly limited, so long as it can retain a measurement sample or a reference liquid on the electrodes. It may be a well formed by an insulating material, or a space formed by two or more laminated insulating materials. Preferably, a resist film having a liquid reservoir form is formed on a cover plate composed of an insulating material film provided with a sample-feeding hole, a air ventilation hole, a bridge hole and holes for exposure of terminals, and the resist film is bonded to a substrate on which the aforementioned ion-selective film has been formed to form a liquid reservoir with the resist film of the substrate, the cover plate and the resist film of the cover plate. The ion activity-measuring device that has such a liquid reservoir can be in a plate-like form, and it is preferred as a disposable ion activity-measuring device.

On the side of the electrodes of the ion activity-measuring device, there may be provided a protective film that can be easily peeled upon use. Further, indication of the mounting direction on an apparatus for ion activity measurement may be printed. Furthermore, on the back surface, identification codes such as bar codes may be printed.

The ion activity-measuring device of the present invention comprises a hydrophobic bridge of which portion contacting with a liquid reservoir is hydrophilic. This bridge may be hydrophilic for the entire portion contacting with a liquid reservoir, or only a part of it, i.e., a tip end of it may be hydrophilic.

While a member constituting the hydrophobic bridge is not particularly limited so long as a liquid can permeate it, examples thereof include porous members such as non-woven fabric and textile fabric. Examples of a material of the member constituting the bridge include a hydrophobic polymer. This material is preferably one which can be fused to the cover plate. Specific examples of the hydrophobic polymer are polyesters (e.g., polyethylene terephthalate), nylon, polypropylene, rayon, polyethylene and so forth.

The bridge having the above structure can be produced by treating the portion contacting with the liquid reservoir with a spreading accelerator. Alternatively, it can also be constituted by a hydrophobic porous member and hydrophilic porous members that are disposed on the both sides of the hydrophobic porous member so that they should be in contact with the hydrophobic porous member. In view of the simplicity of the production method, the portion contacting with the liquid reservoir is preferably constituted by the hydrophobic porous member treated with the spreading accelerator.

The spreading accelerator is not particularly limited, so long as the hydrophobic polymer can be made hydrophilic by treatment with it. Examples thereof include a surfactant and a hydrophilic polymer. As the surfactant, it is preferable to use a nonionic surfactant in view of the influence on the measurement of ion activity. When the measurement is performed for a sample containing blood cells, it is preferable to use a nonionic compound such as Triton X-405 (trade name) and lecithin, which exhibit little influence such as disruption of the blood cells. As the hydrophilic polymer, it is possible to use polyvinyl alcohol or polyvinylpyrrolidone (e.g., PVPK15 (trade name)). The surfactant and the hydrophilic polymer may be used each alone or in combination. Further, one kind of each may be used or two or more kinds of each may be used in combination.

The treatment with the spreading accelerator can be performed by soaking the both ends of the bridge with a solution of the spreading accelerator in a suitable solvent by spraying, coating, dipping, point deposition etc., and drying it. By the treatment with the spreading accelerator, the treated portion is made hydrophilic. The amount of the spreading accelerator required for imparting the hydrophilicity can be easily determined by those skilled in the art.

The bridge having the above structure is preferably bonded to the cover plate by fusion using an ultrasonic fusion machine. In this case, by using an ultrasonic fusion machine having a knurled horn tip end, bonding of further higher adhesion strength can be attained.

The reason why the reproducibility of the ion activity measurement method utilizing the ion activity-measuring device of the present invention is improved is presumed as follows. Since conventional bridges are constituted by a uniform material along the direction of liquid permeation, the fronts of the liquids permeated from the first liquid reservoir and the second liquid reservoir are not uniform in many cases, and this is considered to invite partial contact or mixing of the liquids. On the other hand, in the bridge of the ion activity-measuring device of the present invention, since a 3-part structure of hydrophilic portion/hydrophobic portion/hydrophilic portion is formed between the first liquid reservoir and the second liquid reservoir along the direction of liquid permeation, the liquids on the both liquid reservoirs permeate into the hydrophilic portions first, but do not reach the center portion at once due to the hydrophobicity of the center portion. Then, after a sufficient amount of the liquids are retained in the hydrophilic portions, the liquids advance toward the hydrophobic portion at a stretch and the both liquids are brought into contact with each other. For this reason, it is considered that, in the ion activity-measuring device of the present invention, there are suppressed the partial contact and mixing of the liquids, which are considered to adversely affect the reproducibility of ion activity measurement, and thus the reproducibility is improved.

Figure 1:
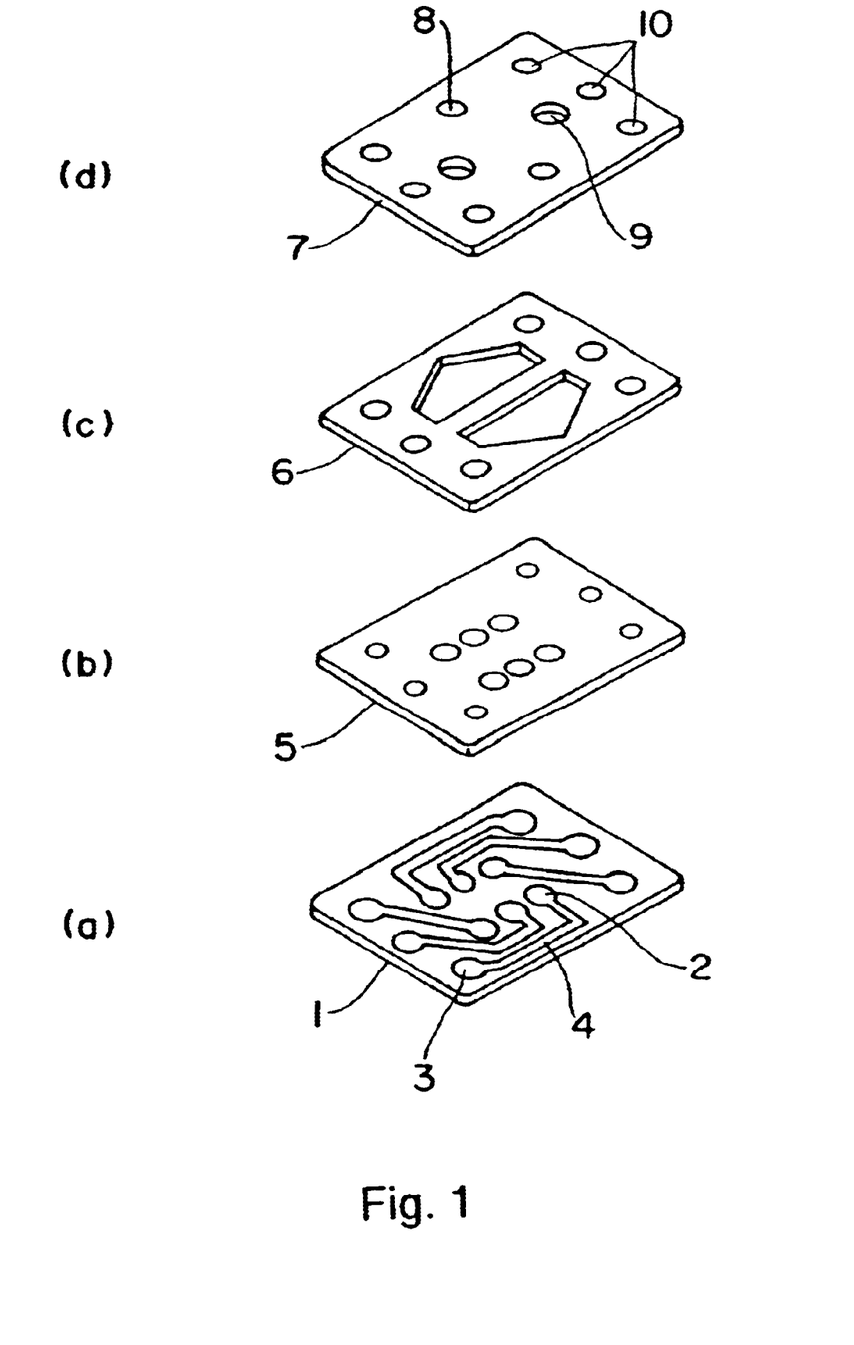
FIG. 1 shows an exploded perspective view of an ion activity-measuring device.

Hereafter, an ion activity-measuring device of plate-type will be explained as an example of the ion activity-measuring device of the present invention with reference to FIG. 1. FIG. 1 is an exploded perspective view of the ion activity-measuring device In this ion activity-measuring device, a substrate 1, on which electrode metal layers constituting three pairs of electrodes and each composed of an electrode portion 2, a terminal portion 3 and a lead wire portion 4, a first resist film 5 and an ion-selective film are formed, is adhered to a cover plate 7 composed of a film of an insulating material provided with a sample-feeding hole 8, an air ventilation hole 9 and holes for exposure of terminals 10, on which a second resist film 6 is formed, whereby liquid reservoirs are formed with the first resist film 5, the cover plate 7 and the second resist film 6.

Figure 2:
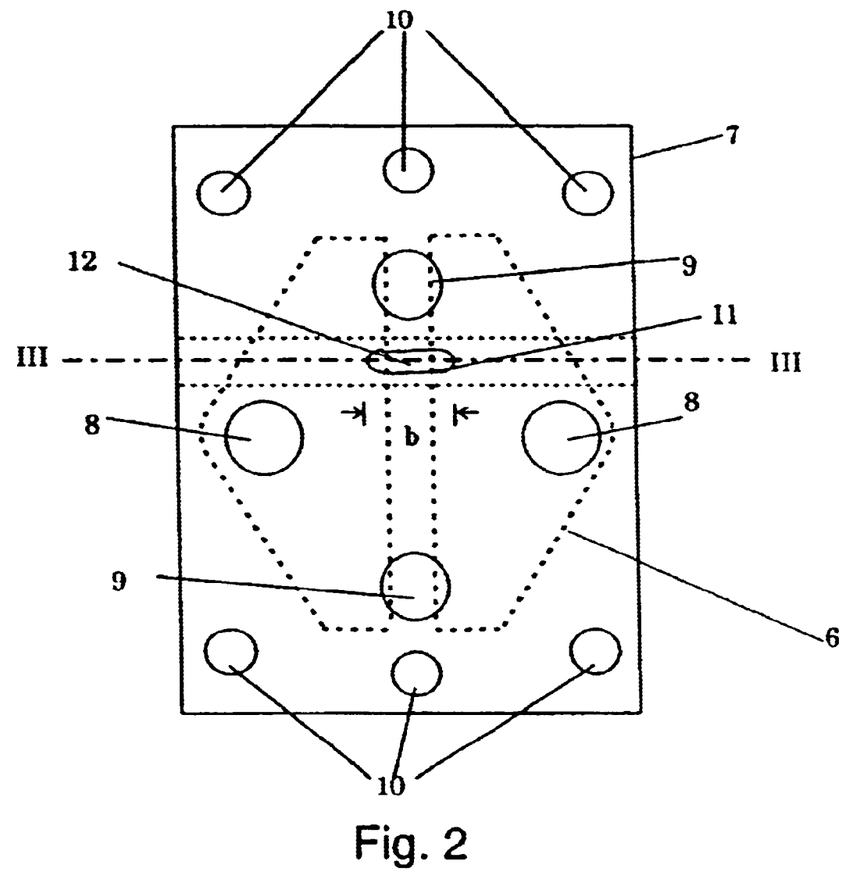
FIG. 2 is a plan view of an exemplary structure of a cover plate having a bridge.
Figure 3:
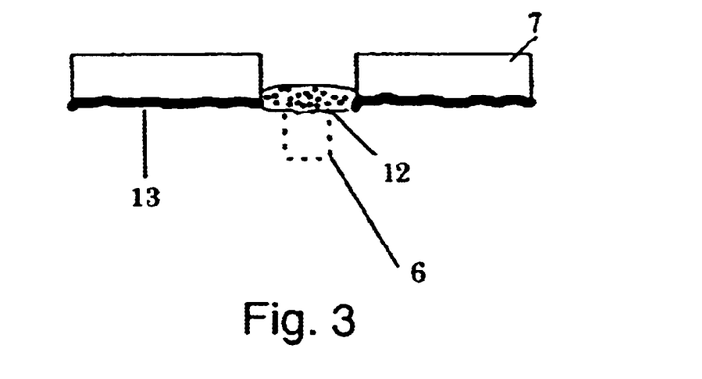
FIG. 3 is a sectional view along the line III—III in FIG. 2.
Figure 4:
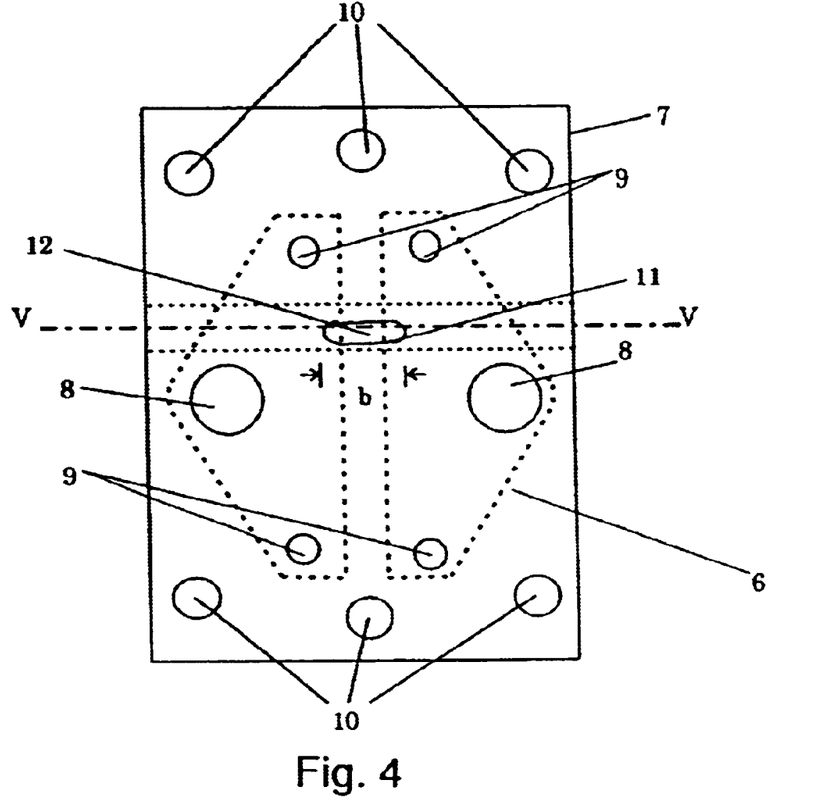
FIG. 4 is a plan view of an exemplary structure of a cover plate having a bridge.
Figure 5:
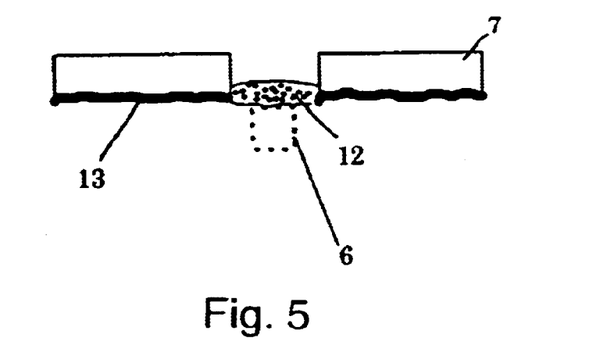
FIG. 5 is a sectional view along the line V—V in FIG. 4.
Figure 6:
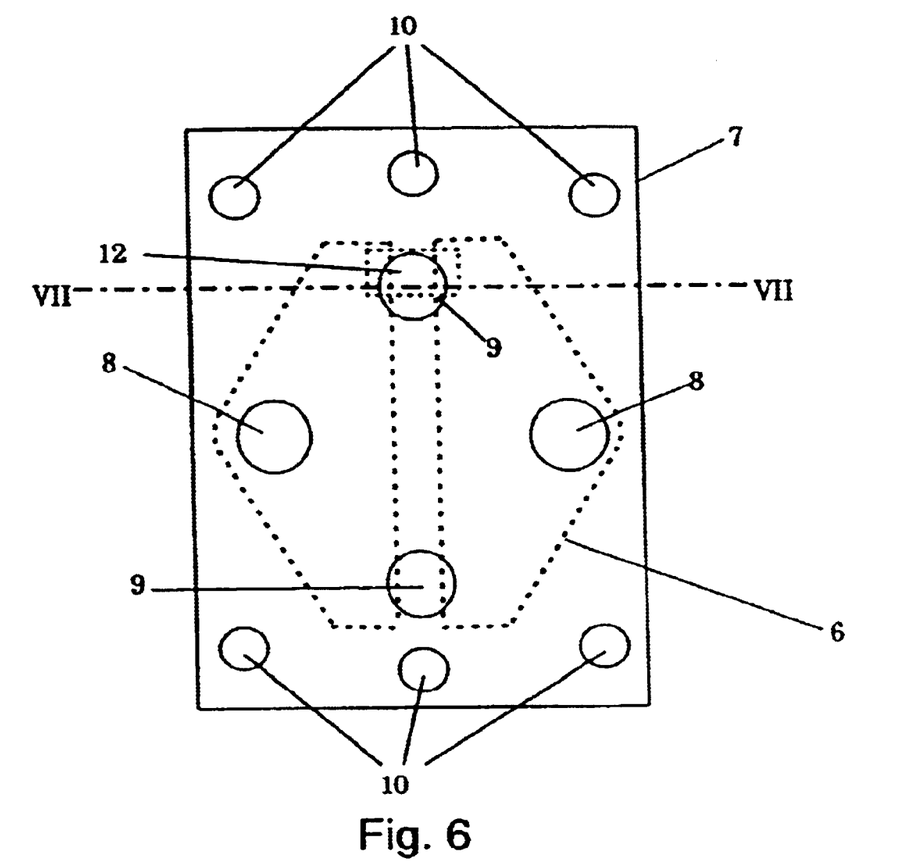
FIG. 6 is a plan view of an exemplary structure of a cover plate having a bridge.
Figure 7:
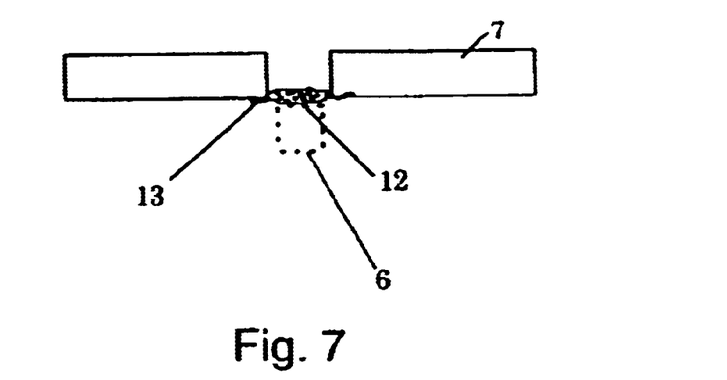
FIG. 7 is a sectional view along the line VII—VII in FIG. 6.

Examples of the structure of the cover plate having a bridge is shown in FIGS. 2 to 7. FIGS. 2, 4 and 6 are plan views, and FIGS. 3, 5 and 7 are sectional views along the lines of III—III, V—V and VII—VII in FIGS. 2, 4 and 6, respectively.

In the example shown in FIG. 2, nonwoven fabric or textile fabric is disposed as a bridge material (porous member) so as to cover a hole for bridge 11, and fused to the cover plate 7. Referring to FIG. 3, a portion of the nonwoven fabric or textile fabric contacting with the cover plate 7 is fused, and the portion not fused due to the presence of the hole for bridge 11 serves as a bridge 12.

The width b of the hole for bridge should be larger than the width of a separator that is a portion separating the first liquid reservoir and the second liquid reservoir of the second resist, so that flows of liquids from the liquid reservoirs should not be prevented.

In the example shown in FIG. 2 where the air ventilation hole 9 is commonly used for the first liquid reservoir and the second liquid reservoir, the width of the air ventilation hole is wider than the width of the separator of the second resist 6.

The air ventilation hole 9 may also be provided for each of the first liquid reservoir and the second liquid reservoir as shown in FIG. 4. In this case, the size of the air ventilation hole 9 need not be larger than the width of the separator of the second resist 6.

Further, as shown in FIG. 6, the air ventilation hole 9 may also serve as the hole for bridge. In this embodiment, the bridge 12 is disposed so that it should cover a part of the area of the air ventilation hole 9 and thus the air ventilation of the liquid reservoirs should be possible.

The fusion of the nonwoven fabric or textile fabric to the cover plate 7 can be attained by ultrasonic wave or heating. The length to be fused of the nonwoven fabric or textile fabric used for the bridge 12 may be the same as that of the plate as shown in FIGS. 2 or 4, or it may be a part of the length as shown in FIG. 6. However, it should be longer than the size of the hole for bridge. The thickness of the nonwoven fabric or textile fabric is usually 30 to 200 $\mu$m, more preferably 50 to 150 $\mu$m.

Further, a commonly used hole for bridge as shown in FIG. 6 may be used with nonwoven fabric or textile fabric fused over the full length of the plate as shown in FIG. 2 or 4, or a independent hole for bridge as shown in FIG. 2 or 4 may be used with nonwoven fabric or textile fused for a partial length as shown in FIG. 6.

As for the aforementioned bridge material, when the spreading of liquid shows anisotropy in it, mixing state and mixing rate of a standard liquid (reference liquid) and a measurement liquid (liquid sample) in the bridge, which are important factors for stability of electric response potential, can be controlled by selecting the direction of the fusion of the material.

An example of the method for producing an ion activity-measuring device will be explained with reference to FIG. 1.

First, as shown in FIG. 1(a), a conductive metal paste (preferably silver paste) is applied to the substrate 1 made of a plastic film by a conventional method such as printing to form metal layers of an electrode pattern composed of an electrode portion 2, a terminal portion 3 and a lead wire portion 4 connecting the electrode portion 2 and the terminal portion 3. A portion to be the electrode portion 2 may be converted into silver halide by chemical treatment in this stage, but such chemical treatment is preferably performed after the first resist film S is formed. If a layer of a non-conductive material is provided at the contact portion of the metal layer for electrode and the first resist film 5 (i.e., a portion around the electrode portion 2) before forming the first resist film 5, it will be advantageous for forming a uniform ion-selective film.

Then, on the substrate 1 on which the metal layers for electrode are formed, the first resist layer 5 in a form covering portions other than the electrode portions 2 and the terminal portions 3, as shown in FIG. 1(b), is formed.

In this stage, a predetermined amount of a solution of the ion-selective film material is poured into the regions surrounded by the first resist layer 5 over the electrode portions 2, and dried to form ion-selective films. The ion-selective films are formed on the right and left sides as one pair. In the device shown in the figure, the ion-selective films are formed to contain three kinds of ion carriers. Before the ion-selective films are formed, a predetermined amount of an electrolyte solution may be poured into the regions surrounded by the first resist layer 5 over the electrode portions 2, and dried to form electrolyte layers, and then the ion-selective films may be formed on the formed electrolyte layers.

Separately, a cover plate 7 composed of a plastic film provided with a sample-feeding hole 8, an air ventilation hole 9 and holes for exposure of terminals 10 is prepared as shown in FIG. 1(d), and ribbon-shaped nonwoven fabric made of a hydrophobic polymer is fused to the cover plate so that the nonwoven fabric should cross the air ventilation hole 9, which also serves as a bridge hole.

On this cover plate 7, the second resist layer 6 in such a form that it should form two liquid reservoirs each containing one of a pair of the electrode portions 2 as shown in FIG. 1(c) is formed. The width of the, portion separating two liquid reservoirs (separator) is selected to be narrower than the diameter of the air ventilation hole 9.

A solution of a spreading accelerator is sprayed on the surface provided with the second resist layer 6 so that the exposed nonwoven fabric portion should become hydrophilic, and the surface is dried. As a result, a bridge is formed.

The second resist layer 6 side of the cover plate 7 obtained as described above and the first resist layer 5 side of the substrate 1 on which the aforementioned ion-selective film is formed are adhered to complete the ion activity-measuring device of the present invention. While the above procedure was explained without especially referring to number of the device, a pattern comprising a plurality of ion activity-measuring devices can be formed on one sheet of film according to the size that can be printed by a screen printing machine or the like. In such a case, by cutting the film in a final step, a plural of ion activity-measuring devices of the present invention can be produced simultaneously.

Upon measurement, a liquid sample of which ion activity is to be measured and a reference liquid of a predetermined ion activity are supplied from one of sample-feeding holes and the other, respectively, substantially at the same time. The supplied liquid sample and the reference liquid spread over the entire volume of the spaces formed by the cover plate, the first resist layer and the second resist layer (liquid reservoirs) by capillarity, contact with each electrode, and permeate the bridge to provide electric conduction between the both liquid reservoirs.

As a result, an electric cell is formed between each pair of the electrodes. Its electromotive force can be measured and a concentration can be calculated based on a calibration curve prepared beforehand.

In a preferred method for producing the ion activity-measuring device of the present invention, a porous member is provided on a member which constitutes a liquid reservoir and has a hole for bridge; a separator is provided thereon so that the separator should cross over the hole for bridge; and then a spreading accelerator is sprayed to treat an exposed portion of the porous member with the spreading accelerator to form a bridge.

The member that has the hole for bridge is usually the aforementioned cover plate. The separator is a member for separating the first liquid reservoir and the second liquid reservoir, and usually formed as a part of the second resist. By spraying the spreading accelerator after the separator is provided, only the both ends of the porous member are treated with the spreading accelerator, and a three-part structure of hydrophilic part/hydrophobic part/hydrophilic part can easily be obtained. Therefore, this production method is suitable for mass production of the ion activity-measuring device of the present invention.

Further, it is preferable to form a bridge by disposing a porous material of a ribbon-like shape (bridge material) for the full length of the plate, and fusing it to the cover plate. When the ion activity-measuring devices of the present invention are produced in a large scale by cutting out from one sheet of film in a final step according to this embodiment, the positioning and fusion of the porous material become easy according to this embodiment. Therefore, mass production becomes easy.

In an embodiment of the ion activity-measuring device of the present invention, i.e., an embodiment where liquid reservoirs are formed by bonding a cover plate and a substrate, at least one of which has a resist film having a liquid reservoir form, and the hydrophobic bridge is made of nonwoven fabric, the nonwoven fabric in the shape of a sheet, produced from polyester, nylon, polyvinylene, rayon, polyethylene or the like, as a member constituting the hydrophobic bridge is bonded to the cover plate.

For the bonding in this case, while heat fusion attained by heating or bonding with an adhesive may be generally used, the nonwoven fabric is preferably embedded in the cover plate to bond the nonwoven fabric to the cover plate.

The bonding of the cover plate and the nonwoven fabric is attained by overlaying the nonwoven fabric on the cover plate. When heat fusion is used for the bonding, the overlapped portion has a structure having a thickness of the nonwoven fabric, and therefore it has a level difference with respect to the cover plate. When an adhesive is used for the bonding, the thickness of the applied adhesive is added to the thickness of the nonwoven fabric itself.

The liquid sample and the reference liquid are each added to separate liquid reservoirs to fill the liquid reservoirs with the liquids. Since the liquid sample and the reference liquid are added at a relatively high speed by using a pipet or the like, an air layer may be formed at the portion having the level difference between the cover plate and the nonwoven fabric. Thus, there may be observed a phenomenon that the liquid sample and the reference liquid are not spread over the bridge, or they are difficult to spread.

Further, if the cover plate and the nonwoven fabric are bonded only by heat fusion, the nonwoven fabric may be easily peeled when a force is applied to the fused portion. Therefore, there is also a risk that the bridge may be peeled due to drop thereof during transportation or use of the device for ion activity measurement, and thus the device becomes unusable.

If the nonwoven fabric is embedded in the cover plate and bonded to it, the level difference between the cover plate and the bridge is reduced. Thus, an air layer is not formed upon addition of the liquid sample and reference liquid, and bonding strength is also improved. Therefore, the aforementioned problem can be solved.

In order to embed the nonwoven fabric in the cover plate, it is effective to attain the bonding by heating and pressing the portion overlapped with the nonwoven fabric to push the thickness of the nonwoven fabric into the cover plate as much as possible.

As such a bonding method, there can be mentioned a heat fusion. The heat fusion includes the heating fusion method, ultrasonic fusion method and high frequency fusion method. In these methods, bonding is attained by directly applying heat or generating heat to melt a member to be fused, and applying a certain level of pressure.

The heating fusion method is a method for bonding by directly applying heat to a part to be fused. Since the heat is applied to a portion other than the portion desired to be fused in this method, it requires certain means for preventing distortion of the cover plate upon pressing.

The high frequency fusion method is a method for bonding by vibrating metal particles of aluminum or the like present in the member to be fused to generate heat and melting the member by the generated heat. This method is required to prepare nonwoven fabric or a PET film by mixing metal particles such as those of aluminum.

Therefore, the preferred fusion method for the present invention is the ultrasonic fusion method. In the ultrasonic fusion, bonding is attained by using a horn conducting a supersonic wave, which is brought into contact with a portion to be fused to melt a member to be fused at each surface.

Most preferably, bonding is attained by knurled fusion based on the ultrasonic fusion.

The knurled fusion is a bonding method in which a knurled horn provided at the tip end of a fusion machine is used; a knurled portion vibrated with an ultrasonic wave melts a member to be fused; and a certain level of pressure is applied. Thus, a surface of the member to be fused contacting with the knurled portion is finished to have a knurled pattern.

While the nonwoven-fabric can be embedded in the cover plate by such bonding as described above, the entire nonwoven fabric is not necessary to be embedded in the cover plate, and it may be sufficient if there is obtained the effect of facilitating spreading of the liquid sample and the reference liquid by reducing the level difference due to the thickness of the nonwoven fabric.

The bonding strength between the fused cover plate and nonwoven fabric may vary depending on the thickness. In order to maintain the strength, the thickness of the cover plate is preferably 50 to 250 $\mu$m, and the thickness of the nonwoven fabric is preferably 30 to 150 $\mu$m.

EXAMPLES

Hereafter, the present invention will be specifically explained with reference to the following examples.

Example 1

An ion activity-measuring device for simultaneously measuring each of Na, K and Cl ions was prepared by the following process steps.

Step 1. Patterns each composed of an electrode portion, a terminal portion and a lead wire portion connecting the electrode portion and the terminal portion were printed with a thermosetting silver paste (VO-200, produced by Acheson Japan) through a screen of 200 mesh with a thickness of 20 $\mu$m on a polyester film so as to form three pairs of electrodes, and then the paste was cured by heating at 150° C. for 30 minutes to form silver layers.

Step 2. An ultraviolet curing type resist,(ML-25089, produced by Acheson Japan) was printed on the contact portions of a resist film and the electrode portions through a screen of 300 mesh and a thickness of 10 $\mu$m and cured by ultraviolet radiation.

Step 3. An ultraviolet curing type resist was printed on portions other than the terminal portions and electrode positions through a screen of 300 mesh and a thickness of 40 $\mu$m and cured by ultraviolet radiation. This procedure was repeated 3 times to form a resist film with a thickness of about 50 $\mu$m.

Step 4. The polyester film was immersed in 3 N nitric acid aqueous solution for 1 minute and washed.

Step 5. The polyester film was immersed in a chromic acid solution (1% dichromic acid, 0.15 N hydrochloric acid, 0.2 N potassium chloride) for 3 minutes and washed to form a silver chloride layer.

Step 6. A solution of each ion-selective film material, of which composition is shown in Table 1, was added dropwise to holes in an amount of 0.7 $\mu$l per hole and dried to form an ion-selective film.

TABLE 1

| Composition of ion-selective film | | | |
|---|---|---|---|
| | Na | K | Cl |
| Polyvinyl chloride (Aldrich) | 8.00 | 8.00 | 8.00 |
| Dioctyl adipate (Wako Pure Chemicals) | 27.00 | 28.00 | 17.00 |
| NaTFPB1[1] (Dojin Chemical) | 0.05 | | |
| B124[2] (Dojin Chemical) | 0.60 | | |
| KTCPB[3] (Dojin Chemical) | | 0.05 | |
| Valinomycin (Calbiochem) | | 0.35 | |
| Capriquat[4] (Dojin Chemical) | | | 8.00 |
| Tetrahydrofuran (Nakarai Tesque) | 64.35 | 63.60 | 67.00 |

[1] Sodium tetrakis[3,5-bis(trifluoromethyl)phenyl]borate
[2] Bis[(12-crown-4)methyl]-2-dodecyl-2-methylmalonate
[3] Potassium tetrakis(p-chlorophenyl)borate
[4] Tri-n-octylmethylammonium chloride Step 7. A polyester film provided with a sample-feeding hole, an air ventilation hole, holes for exposure of terminal portions and a bridge hole was prepared, and polyethylene terephthalate nonwoven fabric (MF-80K (trade name), produced by Japan Vilene, thickness: 100 $\mu$m) was disposed over the bridge hole and fused.

As the nonwoven fabric, nonwoven fabric in a ribbon-like shape having a thickness of 100 $\mu$m and a width of 2 mm was used. The polyester film was made of polyethylene terephthalate, and had a thickness of 188 $\mu$m and a size of 16×17 cm.

After the ribbon-like nonwoven fabric was fitted approximately on the center of the bridge hole, the polyester film and the nonwoven fabric were fused by using an ultrasonic fusion machine, Branson Ultrasonic Wave Plastic Assembly System 947D (produced by Emerson Japan, fusion conditions: frequency of 40 kHz, fusion time of 0.12 seconds and pressure of 1.0 kgf/cm$^2$).

The tip end of a horn used for the aforementioned ultrasonic fusion machine was one subjected to knurling with a size of 0.3 mm (mesh) for an area of 24×5 mm.

Step 8. An ultraviolet curing type resist was printed in a pattern for forming liquid reservoirs through a screen of 300 mesh with a thickness of 40 $\mu$m and cured by ultraviolet radiation. This procedure was repeated 3 times to form a resist film with a thickness of about 50 $\mu$m.

Step 9. A solution of a surfactant and a hydrophilic polymer .(water:Triton X-405:PVPK15=98.5:1.0:0.5 (weight ratio)) was sprayed on the surface of the polyester film on which the resist film had been formed in an amount of 1.0 mg/cm$^2$, and the polyester film was dried, whereby only the portions of the bridge not covered by the resist film were treated with the surfactant and the hydrophilic polymer.

Step 10. The polyester films obtained in the above 6 and 9 were bonded and cut into a predetermined size to obtain an ion activity-measuring device.

Example 2

An ion activity-measuring device was obtained in the same manner as in Example 1 except that the process step 7 in Example 1 was modified as follows.

Step 7. A polyester film provided with a sample-feeding hole, an air ventilation hole and holes for exposure of terminal portions was prepared, and polyethylene terephthalate nonwoven fabric in a ribbon-like shape (MF-80K (trade name), produced by Japan Vilene., thickness: 80 $\mu$m) was fused so that it should cross the air ventilation holes for each electrode to form a bridge.

Comparative Example 1

An ion activity-measuring device was obtained in the same manner as in Example 1 except that the process step 9 was not performed.

Comparative Example 2

An ion activity-measuring device was obtained in the same manner as in Example 1 except that silk twisted yarn (Y-KT2510 (trade name), produced by Kyo Sakura, diameter: 80 $\mu$m) was used as the material of the bridge and the process step 9 was not performed.

Test Example

The measurement of ion activity of human blood serum was performed by using an electrode type electrolyte analyzer (Spotchem (trade mark) SE-1510, Kyoto Dai-ichi Kagaku) equipped with one of the ion activity-measuring devices obtained in Examples 1 and 2 and Comparative Examples 1 and 2. The measurement was performed 7 times, and standard-deviations (S.D.) and variation of electric potential were obtained. The results are shown in Table 2.

TABLE 2

| | Measured values for 60 seconds | | | | | |
|---|---|---|---|---|---|---|
| | S.D. | | | Variation of electric potential (mV) | | |
| | Na | K | Cl | Na | K | Cl |
| Example 1 | 0.16 | 0.13 | 0.20 | 0.46 | 0.42 | 0.56 |
| Example 2 | 0.18 | 0.15 | 0.19 | 0.48 | 0.42 | 0.52 |
| Comparative Example 1 | 0.53 | 0.28 | 0.41 | 1.54 | 0.78 | 1.20 |
| Comparative Example 2 | 0.24 | 0.19 | 0.25 | 0.68 | 0.60 | 0.72 |

As clearly shown by the above results, when the ion activity-measuring devices of the present invention were used, the standard deviation and the variation o,f electric potential were smaller. Thus, it have been found that the reproducibility of the ion activity measurement using the ion activity-measuring device of the present invention is excellent.

Industrial Applicability

According to the ion activity-measuring device of the present invention utilizing dry-type electrodes, ion activity can be measured with good reproducibility. Further, according to the ion activity-measuring device of the present invention, the,production method therefor can be simplified and it can be readily produced in an integrated production line. Therefore, it enables cost reduction.

What is claimed is:

1. An ion activity-measuring device for measuring activity of an ion in a sample, which comprises at least one pair of electrodes, one of the electrodes being to contact with a liquid sample, and the other being to contact with a reference liquid, a first liquid reservoir for the liquid sample, a second liquid reservoir for the reference liquid, and a hydrophobic bridge of which portions contacting with the liquid reservoirs are hydrophilic, wherein the device is adapted to supplying the liquid sample and the reference liquid substantially at the same time, and wherein the hydrophobic bridge is produced by treating the portions contacting with the liquid reservoirs with a spreading accelerator.

2. The ion activity-measuring device according to claim 1, wherein the hydrophobic bridge is produced from at least one selected from the group consisting of polyester, nylon, polypropylene, rayon and polyethylene.

3. The ion activity-measuring device according to claim 1, wherein the spreading accelerator is at least one selected from the group consisting of a surfactant and a hydrophilic polymer.

4. The ion activity-measuring device according to claim 1, wherein the liquid reservoirs are formed by bonding a cover plate and a substrate, at least one of which has a resist film having a liquid reservoir form, and the hydrophobic bridge is made of nonwoven fabric.

5. A method for producing the ion activity-measuring device as defined in claim 4, comprising embedding nonwoven fabric in the cover plate to bond the nonwoven fabric to the cover plate.

6. The method according to claim 5, wherein the nonwoven fabric and the cover plate are bonded by ultrasonic fusion.

7. The method according to claim 5, wherein the nonwoven fabric and the cover plate are bonded by knurling fusion.

* * * * *